(12) United States Patent
Freudenberger

(10) Patent No.: US 6,965,032 B2
(45) Date of Patent: Nov. 15, 2005

(54) SUBSTITUTED DIHYDRO 3-HALO-1H-PYRAZOLE-5-CARBOXYLATES AND THEIR PREPARATION AND USE

(75) Inventor: John Herbert Freudenberger, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 44 days.

(21) Appl. No.: 10/482,458

(22) PCT Filed: Aug. 13, 2002

(86) PCT No.: PCT/US02/25614

§ 371 (c)(1),
(2), (4) Date: Dec. 30, 2003

(87) PCT Pub. No.: WO03/016283

PCT Pub. Date: Feb. 27, 2003

(65) Prior Publication Data

US 2004/0198987 A1 Oct. 7, 2004

Related U.S. Application Data

(60) Provisional application No. 60/369,660, filed on Apr. 2, 2002, provisional application No. 60/341,958, filed on Dec. 19, 2001, and provisional application No. 60/311,919, filed on Aug. 13, 2001.

(51) Int. Cl.[7] ..................... C07D 231/06; C07D 403/04
(52) U.S. Cl. ................. 546/275.4; 546/276.1; 548/379.4
(58) Field of Search ............................ 546/275.4, 276.1; 548/379.4

(56) References Cited

U.S. PATENT DOCUMENTS

| 3,153,654 A | 10/1964 | Ficken et al. |
| 5,945,541 A | 8/1999 | Sohn et al. |
| 2003/0229050 A1 | 12/2003 | Lahm et al. |

FOREIGN PATENT DOCUMENTS

| EP | 0 333 131 A | 9/1989 |
| JP | 9-17 6124 | 7/1997 |
| JP | 9-31 6055 | 12/1997 |
| NL | 9 202 078 A | 6/1994 |
| WO | WO 01/70671 A | 9/2001 |
| WO | WO 03/015519 | 2/2003 |
| WO | WO 03/016 282 | 2/2003 |

OTHER PUBLICATIONS

U.S. Appl. No. 10/698,643, filed Oct. 31, 2003, Lahm et al.
U.S. Appl. No. 10/483,168, filed Jan. 7, 2004, Lahm et al.
U.S. Appl. No. 10/482,556, filed Dec. 30, 2003, Annis et al.
F. Foti et al., Tetrahedron Letters, First Synthesis of a Bromonitrilimine. Direct Formation of 3-Bromopyrazole Derivatives., 1999, vol. 40, pp. 2605–2605.

Donald J.P. Pinto et al., "Discovery of 1-[3-(Aminomethyl)phenyl]-N-[3-fluoro-2'-(methylsulfonyl)-[1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa1", J. Med. Chem., 2001, vol. 44, pp. 566–578.

M. V. Gorelik et al., "Structure and Properties of . . . ", Journal of Organic Chemistry U.S.S.R. (English) 1985, 21, 773–781.

K. K. Bach et al., "1,3-Dipolar Cycloadditions of . . . ", Tetrahedron 1994, 50(25), 7543–7556.

J. P. Chupp, "New Regional Isomers of . . . ", J. Heterocyclic Chem. 1994, 31, 1377–1380.

*Primary Examiner*—Joseph K. McKane
*Assistant Examiner*—Andrew B. Freistein

(57) ABSTRACT

This invention relates to a compound of Formula I, a method for its preparation and its use in the preparation of a compound of Formula II wherein $R_1$, $R_2$, $R_3$, X and n are as defined in the disclosure. This invention also discloses preparation of compounds of Formula III wherein $R_1$, $R_2$, $R_6$, $R_7$, $R_8$ and n are as defined in the disclosure. Also disclosed are certain intermediates of Formula 4 for the preparation of compounds of Formula I wherein X is N and $R_2$, $R_3$ and n are as defined in the disclosure.

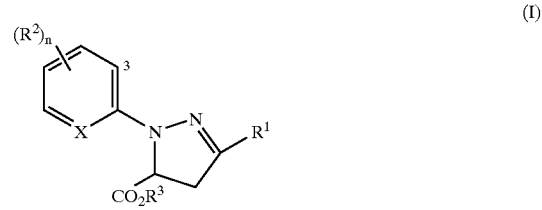

(I)

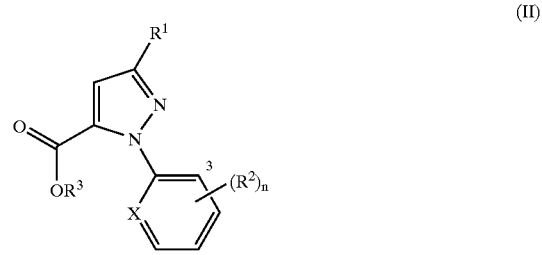

(II)

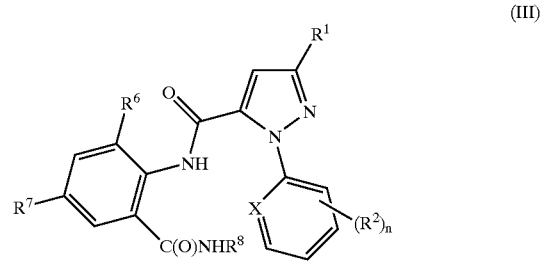

(III)

8 Claims, No Drawings

US 6,965,032 B2

SUBSTITUTED DIHYDRO 3-HALO-1H-PYRAZOLE-5-CARBOXYLATES AND THEIR PREPARATION AND USE

This application is a 371 of PCT/US02/25614 filed Aug. 13, 2002 in English which claims benefit of 60/311,919, filed Aug. 13, 2001, 60/341,958, filed Dec. 19, 2001, and 60/369,660, filed Apr. 2, 2002.

FIELD OF THE INVENTION

This invention relates to novel carboxylic acid derivatives of 3-halo-1-aryl-substituted dihydro-1H-pyrazoles and pyrazoles. These compounds are useful for preparation of certain anthranilic amide compounds that are of interest as insecticides (see e.g. PCT Publication WO 01/070671).

BACKGROUND OF THE INVENTION

*Tetrahedron Letters*, 1999, 40, 2605–2606 discloses preparation of 1-phenyl-3-bromopyrazole-5-carboxylic acid derivatives involving generation of a reactive bromonitrilimine intermediate. Cycloaddition of this intermediate with an acrylic ester gives a 1-phenyl-3-bromo-2-pyrazoline-5-carboxylate ester, which can be subsequently oxidized to the desired 1-phenyl-3-bromo-2-pyrazole-5-carboxylate ester. Alternatively, cycloaddition with a propiolate ester gives the 1-phenyl-3-bromo-2-pyrazole-5-carboxylate ester directly.

U.S. Pat. No. 3,153,654 discloses condensation of certain optionally substituted aryl (e.g. phenyl or naphthyl which are optionally substituted with lower alkyl, lower alkoxy or halogen) hydrazines with certain fumaric or maleic esters to provide 3-pyrazolidinone carboxylic acid derivatives.

Japanese Unexamined Patent Publications 9-316055 and 9-176124 disclose production of pyrazole carboxylic acid ester derivatives and pyrazoline derivatives, respectively, which are substituted with alkyl at the 1-position.

*J. Med. Chem.* 2001, 44, 566–578 discloses a preparation of 1-(3-cyanophenyl)-3-methyl-1H-pyrazol-5-carboxylic acid and its use in preparing inhibitors of blood coagulation factor Xa.

The present invention provides technology useful for conveniently preparing 3-halo-5-carboxylate-1-aryl-substituted dihydro-1H-pyrazoles and pyrazoles.

SUMMARY OF THE INVENTION

This invention relates to a compound of Formula I

I wherein
  $R^1$ is halogen;
  each $R^2$ is independently $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;
  $R^3$ is H or $C_1$–$C_4$ alkyl;
  X is N or $CR^4$;
  $R^4$ is H or $R^2$; and
  n is 0 to 3, provided when X is CH then n is at least 1, This invention also relates to a method for preparing a compound of Formula I comprising (1) treating a compound of Formula 4

4

(wherein X, $R^2$, and n are as described above for Formula I and $R^3$ is $C_1$–$C_4$ alkyl) with a halogenating agent to form a compound of Formula I; and when preparing compounds of Formula I wherein $R^3$ is H, (2) converting the compound formed in (1) to a compound wherein $R^3$ is H.

This invention also relates to a compound of Formula II

II wherein $R^1$ is halogen (and X, $R^2$, $R^3$ and n are defined as above for Formula I) and a method of preparing a compound of Formula II. The method comprises (3) treating a compound of Formula I with an oxidant, optionally in the presence of an acid, to form a compound of Formula II; and when a compound of Formula I wherein $R^3$ is $C_1$–$C_4$ alkyl is used to prepare a compound of Formula II wherein $R^3$ is H, (4) converting the compound formed in (2) to a compound of Formula II wherein $R^3$ is H.

This invention also provides compounds of Formula 4 wherein X is N, and their use in preparing compounds of Formulae I and II, wherein X is N (and $R^2$, $R^3$ and n are defined as above for Formula I).

This invention also involves a method of preparing a compound of Formula III,

III wherein X, $R^1$, $R^2$, and n are defined as above for Formula II; $R^6$ is $CH_3$, Cl or Br; $R^7$ is F, Cl, Br, I or $CF_3$; and $R^8$ is $C_1$–$C_4$ alkyl, using a compound of Formula II wherein $R^6$ is H. This method is characterized by preparing the compound of Formula II by the method as indicated above.

DETAILED DESCRIPTION OF THE INVENTION

In the above recitations, the term "alkyl", used either alone or in compound words such as "alkylthio" or "haloalkyl" includes straight-chain or branched alkyl, such as methyl, ethyl, n-propyl, i-propyl, or the different butyl, pentyl or hexyl isomers. "Alkenyl" can include straight-chain or branched alkenes such as 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Cycloalkyl" includes, for example, cyclopropyl, cyclobutyl, cyclopentyl and cyclohexyl. "Cycloalkylalkyl" indicates an alkyl group substituted with a cycloalky group and includes, for example, cyclopropylmethyl, cyclobutylethyl, cyclopentylpropyl and cyclohexylmethyl. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)cycloalkylamino" means a cycloalkylamino group where the hydrogen atom is replaced by an alkyl radical; examples include groups such as (alkyl)cyclopropylamino, (alkyl)cyclobutylamino, (alkyl)cyclopentylamino and (alkyl)cyclohexylamino. Preferably the alkyl in (alkyl)cycloalkylamino is $C_1$–$C_4$ alkyl, while the cycloalkyl in cycloalkylamino and (alkyl)cycloalkylamino is $C_3$–$C_6$ cycloalkyl.

The term in this application "aryl" refers to an aromatic ring or ring system or a heteroaromatic ring or ring system, each ring or ring system optionally substituted. The term "aromatic ring system" denotes fully unsaturated carbocycles and heterocycles in which at least one ring of a polycyclic ring system is aromatic. Aromatic indicates that each of ring atoms is essentially in the same plane and has a p-orbital perpendicular to the ring plane, and in which (4n+2) π electrons, when n is 0 or a positive integer, are associated with the ring to comply with Hückel's rule. The term "aromatic carbocyclic ring system" includes fully aromatic carbocycles and carbocycles in which at least one ring of a polycyclic ring system is aromatic (e.g. phenyl and naphthyl). The term "heteroaromatic ring or ring system" includes fully aromatic heterocycles and heterocycles in which at least one ring of a polycyclic ring system is aromatic and in which at least one ring atom is not carbon and can contain 1 to 4 heteroatoms independently selected from the group consisting of nitrogen, oxygen and sulfur, provided that each heteroaromatic ring contains no more than 4 nitrogens, no more than 2 oxygens and no more than 2 sulfurs (where aromatic indicates that the Hückel rule is satisfied). The heterocyclic ring systems can be attached through any available carbon or nitrogen by replacement of a hydrogen on said carbon or nitrogen. More specifically, the term "aryl" refers to the moiety

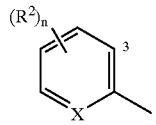

wherein $R^2$ and n are defined as above and the "3" indicates the 3-position for substituents on the moiety.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "aloalkynyl", "haloalkoxy", and the like, are defined analogously to the term "haloalkyl". Examples of "aloalkenyl" include $(Cl)_2C{=}CHCH_2$ and $CF_3CH_2CH{=}CHCH_2$. Examples of "haloalkynyl" include $HC{\equiv}CCHCl$, $CF_3C{\equiv}C$, $CCl_3C{\equiv}C$ and $FCH_2C{\equiv}CCH_2$. Examples of "haloalkoxy" include $CF_3O$, $CCl_3CH_2O$, $HCF_2CH_2CH_2O$ and $CF_3CH_2O$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC({=}O)$, $CH_3CH_2OC({=}O)$, $CH_3CH_2CH_2OC({=}O)$, $(CH_3)_2CHOC({=}O)$ and the different butoxy- or pentoxycarbonyl isomers. The terms "alkylaminocarbonyl" and "dialkylaminocarbonyl" include, for example, $CH_3NHC({=}O)$, $CH_3CH_2NHC({=}O)$ and $(CH_3)_2NC({=}O)$.

The total number of carbon atoms in a substituent group is indicated by the "$C_i$–$C_j$" prefix where i and j are numbers from 1 to 8, For example, $C_1$–$C_3$ alkysulfonyl designates methylsulfonyl through propylsulfonyl. In the above recitations, when a compound of Formula I contains a heteroaromatic ring, all substituents are attached to this ring through any available carbon or nitrogen by replacement of a hydrogen on said carbon or nitrogen.

When a group contains a substituent which can be hydrogen, for example $R^4$, then, when this substituent is taken as hydrogen, it is recognized that this is equivalent to said group being unsubstituted.

Certain compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the compounds of the invention may be present as a mixture of stereoisomers, individual stereoisomers, or as an optically active form.

Preferred for cost, ease of synthesis and/or greatest utility are:

Preferred 1. Compounds of Formula I wherein $R^1$ is Cl or Br;

each $R^2$ is independently Cl or Br, and one $R^2$ is at the 3-position; and

X is N.

Preferred 2. Compounds of Formula I wherein
R¹ is Cl or Br;
X is N; and
n is 0.

Of note are compounds of Formula I (including but not limited to Preferred 1) wherein n is 1 to 3.

Preferred 3. Compounds of Formula II wherein
X is N.

Preferred 4. Compounds of Formula II wherein
R¹ is Cl or Br;
each R² is independently Cl or Br, and one R² is at the 3-position; and
X is N.

Preferred 5. Compounds of Formula II wherein
R¹ is Cl or Br;
X is N; and
n is 0.

Of note are compounds of Formula II (including but not limited to Preferred 3 and Preferred 4) wherein n is 1 to 3.

Preferred 6. Compounds of Formula 4 (wherein R³ is $C_1$–$C_4$ alkyl) wherein each
R² is independently Cl or Br, and one R² is at the 3-position.

Preferred 7. Compounds of Formula 4 (wherein R³ is $C_1$–$C_4$ alkyl) wherein
X is N; and
n is 0.

Of note are compounds of Formula 4 (wherein R³ is $C_1$–$C_4$ alkyl) including but not limited to Preferred 6, wherein n is 1 to 3.

The 3-position is identified by the "3" shown in the aryl moiety included in Formula I, Formula II and Formula 4 above.

Of note are compounds of Formula II wherein when R¹ is Cl or Br, n is 1, and R² selected from Cl or Br is at the 3-position; then X is N. Included are compounds wherein n is from 1 to 3.

Of note are compounds of Formula II wherein when R¹ is Cl or Br, n is 1, and R² selected from Cl or Br is at the 3-position; then X is CR⁴. Included are compounds wherein n is from 1 to 3.

Preferred methods are those comprising the preferred compounds above. Methods of note are those comprising the compounds of note above. Of particular note are a method of preparing a compound of Formula I wherein n is from 1 to 3; and a method of preparing a compound of Formula II wherein n is from 1 to 3.

A stepwise process of preparing compounds of Formula I and Formula II provided herein comprises (a) treating a compound of Formula 2

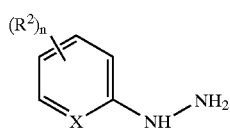

with a compound of Formula 3

wherein R³ is $C_1$–$C_4$ alkyl, in the presence of a base, to form a compound of Formula 4

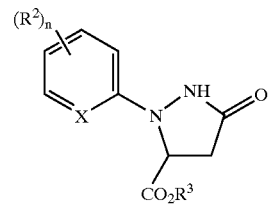

wherein X, R² and n are defined as above and R³ is H; or $C_1$–$C_4$ alkyl. The compound of Formula 4 wherein R³ is $C_1$–$C_4$ alkyl can then be (1) treated with a halogenating agent to form a compound of Formula I; and when preparing compounds of Formula I wherein R³ is H (2) converting the compound formed in (1) to a compound wherein R³ is H.

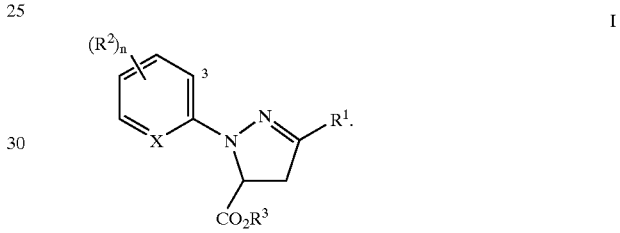

The compound of Formula I prepared in (1) or (2) can then be (3) treated with an oxidant, optionally in the presence of an acid, to form a compound of Formula II; and when compounds of Formula I wherein R³ is $C_1$–$C_4$ alkyl are used to prepare compounds of Formula II wherein R³ is H, (4) converting the compound formed in (3) to a compound of Formula II wherein R³ is H

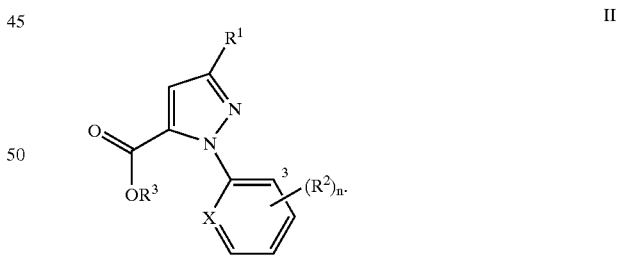

Scheme 1 illustrates step (a).

Scheme 1

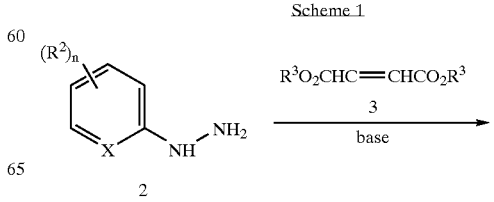

-continued

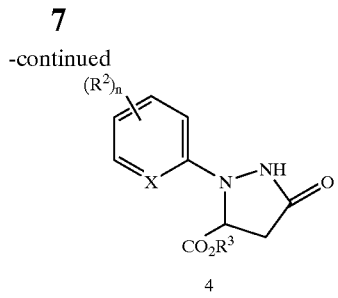

4

In step (a), a compound of Formula 2 is treated with a compound of Formula 3 wherein $R^3$ is $C_1$–$C_4$ alkyl (a fumarate ester or maleate ester or a mixture thereof may be used) in the presence of a base and a solvent. The base is typically a metal alkoxide salt, such as sodium methoxide, potassium methoxide, sodium ethoxide, potassium ethoxide, potassium tert-butoxide, lithium tert-butoxide, and the like. Greater than 0.5 equivalents of base versus the compound of Formula 2 should be used, preferably between 0.9 and 1.3 equivalents. Greater than 1.0 equivalents of the compound of Formula 3 should be used, preferably between 1.0 to 1.3 equivalents. Polar protic and polar aprotic organic solvents can be used, such as alcohols, acetonitrile, tetrahydrofuran, N,N-dimethylformamide, dimethyl sulfoxide and the like. Preferred solvents are alcohols such as methanol and ethanol. It is especially preferred that the alcohol be the same as that making up the fumarate or maleate ester and the alkoxide base. The reaction is typically conducted by mixing the compound of Formula 2 and the base in the solvent. The mixture can be heated or cooled to a desired temperature and the compound of Formula 3 added over a period of time. Typically reaction temperatures are between 0° C. and the boiling point of the solvent used. The reaction may be conducted under greater than atmospheric pressure in order to increase the boiling point of the solvent. Temperatures between about 30 and 90° C. are generally preferred. The addition time can be as quick as heat transfer allows. Typical addition times are between 1 minute and 2 hours. Optimum reaction temperature and addition time vary depending upon the identities of the compounds of Formula 2 and Formula 3. After addition, the reaction mixture can be held for a time at the reaction temperature. Depending upon the reaction temperature, the required hold time may be from 0 to 2 hours. Typical hold times are from about 10 to 60 minutes. The reaction mass then can be acidified by adding an organic acid, such as acetic acid and the like, or an inorganic acid, such as hydrochloric acid, sulfuic acid and the like. Depending on the reaction conditions and the means of isolation, compounds of Formula 4 wherein $R^3$ is H or compounds of Formula 4 wherein $R^3$ is $C_1$–$C_4$ alkyl can be prepared. For example, a compound of Formula 4 wherein $R^3$ is $C_1$–$C_4$ alkyl can be hydrolyzed in situ to a compound of Formula 4 wherein $R^3$ is H when water is present in the reaction mixture. Compounds of Formula 4 wherein $R^3$ is H can be readily transformed to compounds of Formula 4 wherein $R^3$ is $C_1$–$C_4$ alkyl using esterification methods well-known in the art. Compounds of Formula 4 wherein $R^3$ is $C_1$–$C_4$ alkyl are preferred. The desired product, a compound of Formula 4, can be isolated by methods known to those skilled in the art, such as crystallization, extraction or distillation.

In step (1) as illustrated in Scheme 2, a compound of Formula 4 is treated with a halogenating reagent usually in the presence of a solvent. Halogenating reagents that can be used include phosphorus oxyhalides, phosphorus trihalides, phosphorus pentahalides, thionyl chloride, dihalotrialkylphophoranes, dihalodiphenylphosphoranes, oxalyl chloride and phosgene. Preferred are phosphorus oxyhalides and phosphorus pentahalides. To obtain complete conversion, at least 0.33 equivalents of phosphorus oxyhalide versus the compound of Formula 4 should be used, preferably between 0.33 and 1.2 equivalents. To obtain complete conversion, at least 0.20 equivalents of phosphorus pentahalide versus the compound of Formula 4 should be used, preferably between about 0.20 and 1.0 equivalents. Compounds of Formula 4 wherein $R^3$ is $C_1$–$C_4$ alkyl are preferred for this reaction.

Scheme 2

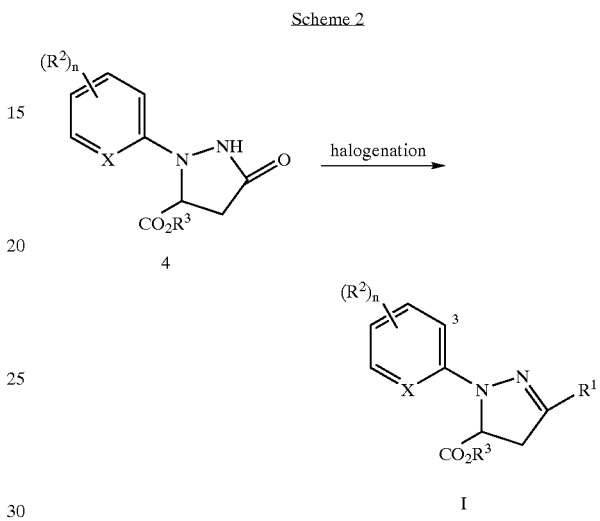

Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula 4 in acetonitrile. The halogenating reagent is then added over a convenient time and the mixture is then held at the desired temperature until the reaction is complete. The reaction temperature is typically between 20° C. and the boiling point of acetontrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula I, can be isolated by methods known to those skilled in the art, including crystallization, extraction and distillation.

In step (2) the compound of Formula I wherein $R^3$ is $C_1$–$C_4$ alkyl, an ester, can be hydrolyzed to a compound of Formula I wherein $R^3$ is H, a carboxylic acid. The hydrolysis can be catalyzed by acids, metal ions, and by enzymes. Iodotrimethylsilane is noted as an example of an acid which can be used to catalyze the hydrolysis (see *Advanced Organic Chemistry*, Third Ed., Jerry March, John Wiley & Sons, Inc. New York, 1985, pp. 334–338 for a review of methods). Base-catalyzed hydrolytic methods are not recommended for the hydrolysis of compounds of Formula I and can result in decomposition. The carboxylic acid can be isolated by methods known to those skilled in the art, including crystallization, extraction and distillation.

In step (3) as illustrated in Scheme 3, a compound of Formula I is treated with an oxidizing agent optionally in the presence of acid. A compound of Formula I wherein $R^3$ is $C_1$–$C_4$ alkyl (i.e. a preferred product of step (1)) is preferred as starting material for step (3). The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula I should be used, preferably from about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula I. To obtain complete conversion, one to five equivalents of acid can be used. For the compounds of Formula I wherein X is $CR^2$, the preferred oxidant is hydrogen peroxide and the oxidation is preferably carried out in the absence of acid. For the compounds of Formula I wherein X is N, the preferred oxidant is potassium persulfate and the oxidation is preferably carried out in the presence of sulfuric acid. The reaction can be carried out by mixing the compound of Formula I in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula II wherein $R^3$ is $C_1$–$C_4$ alkyl, can be isolated by methods known to those skilled in the art, including crystallization, extraction and distillation.

Scheme 3

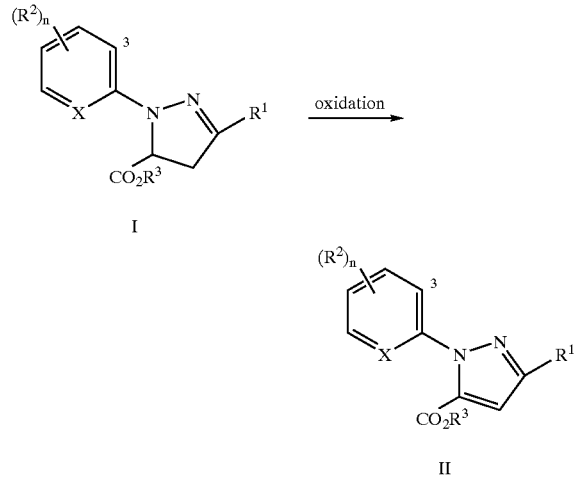

In step (4) as illustrated in Scheme 4, a compound of Formula II wherein $R^3$ is $C_1$–$C_4$ alkyl, an ester, can be converted to a compound of Formula II wherein $R^3$ is H, a carboxylic acid. Methods for converting esters to carboxylic acids are well known to those skilled in the art. Compounds of Formula II ($R^3$ is $C_1$–$C_4$ alkyl) can be converted to compounds of Formula II ($R^3$ is H) by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp. 224–269 for a review of methods). For the method of Scheme 4, base-catalyzed hydrolytic methods are preferred. Suitable bases include alkali metal (such as lithium, sodium or potassium hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid. The carboxylic acid can be isolated by methods known to those skilled in the art, including crystallization, extraction and distillation.

Scheme 4

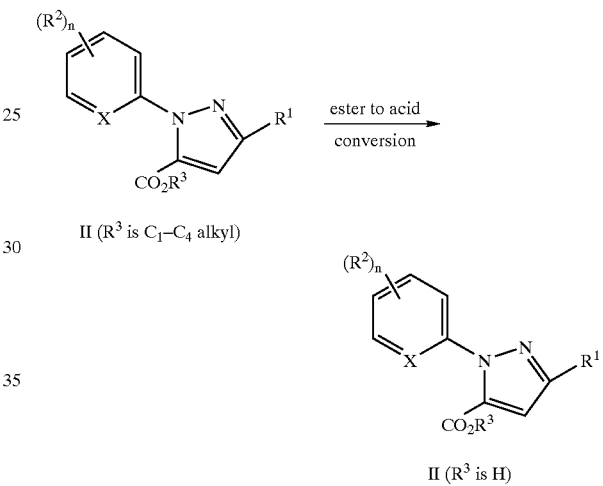

It is noted that certain compounds of Formula I wherein $R^1$ is halogen can be prepared from other compounds of Formula I wherein $R^1$ is a different halogen or is a sulfonate group such as p-toluenesulfonate, benzenesulfonate and methanesulfonate. For example, a compound of Formula I wherein $R^1$ is Br can be prepared by treating with hydrogen bromide the corresponding compound of Formula I wherein $R^1$ is Cl or p-toluenesulfonate. The reaction is conducted in a suitable solvent such as dibromomethane, dichloromethane or acetonitrile. The reaction can be conducted at or near atmospheric pressure or above atmospheric pressure in a pressure vessel. When $R^1$ in the starting compound of Formula I is a halogen such as Cl, the reaction is preferably conducted in such a way that the hydrogen halide generated from the reaction is removed by sparging or other suitable means. The reaction can be conducted between about 0 and 100° C., most conveniently near ambient temperature (e.g., about 10 to 40° C.), and more preferably between about 20 and 30° C. Addition of a Lewis acid catalyst (e.g., aluminum tribromide for preparing Formula I wherein $R^1$ is Br) can facilitate the reaction. The product of Formula I is isolated by the usual methods known to those skilled in the art, including extraction, distillation and crystallization.

Starting compounds of Formula I wherein $R^1$ is halogen can be prepared as already described for Scheme 2. Starting compounds of Formula I wherein $R^1$ is a sulfonate group can likewise be prepared from corresponding compounds of Formula 4 by standard methods such as treatment with a sulfonyl chloride (e.g., p-toluenesulfonyl chloride) and base such as a tertiary amine (e.g., triethylamine) in a suitable solvent such as dichloromethane.

Without further elaboration, it is believed that one skilled in the art using the preceding description can utilize the present invention to its fullest extent. The following Examples are, therefore, to be construed as merely illustrative, and not limiting of the disclosure in any way whatsoever. The starting material for the following Examples may not have necessarily been prepared by a particular preparative run whose procedure is described in other Examples. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet.

EXAMPLE 1

Preparation of Ethyl 5-Oxo-2-phenyl-3-pyrazolidinecarboxylate (alternatively named Ethyl 1-Phenyl-3-pyrazolidinone-5-carboxylate) using Diethyl Maleate To a 300-mL four-necked flask equipped with a mechanical stirrer, thermometer, addition funnel, reflux condenser, and nitrogen inlet was charged 80 mL of absolute ethanol, 80.0 mL (0.214 mol) of 21% sodium ethoxide in ethanol, and 20.0 mL (0.203 mol) of phenylhydrazine. The orange solution was treated dropwise with 40.0 mL (0.247 mol) of diethyl maleate over a period of about 18 minutes. The temperature of the reaction mass rose from 25 to 38° C. during the first 5 minutes of the addition. A water bath was used intermittently throughout the remainder of the addition to moderate the reaction temperature between 38–42° C. The resulting orange-red solution was held under ambient conditions for 30 minutes. It was then added to a separatory funnel containing 20.0 mL (0.349 mol) of glacial acetic acid and 700 mL of water. The mixture was extracted with 250 mL of dichloromethane. The extract was dried over magnesium sulfate, filtered, and then concentrated on a rotary evaporator. The resulting yellow-black oil (52.7 g) was diluted with 100 mL of ether, whereupon crystallization of the product was rapid enough to cause mild boiling. The slurry was held for 2 hours under ambient conditions. It was then cooled to about 0° C. The product was isolated via filtration, washed with 2×20 mL of cold ether, and then air-dried on the filter for about 15 minutes. The product consisted of 29.1 g (61%) of a highly crystalline, white powder. No significant impurities were observed by $^1$H NMR. The filtrate was concentrated to 20.8 g of a brown oil. Analysis of the oil showed the presence of an additional 6.4 g (13%) of the desired product. Hence, the overall yield of the reaction was 74%.

$^1$H NMR (DMSO-d$_6$) δ 10.25 (s, 1H), 7.32 (t, 2H), 7.15 (d, 2H), 7.00 (t, 1H), 4.61 (dd, 1H), 4.21 (q, 2H), 2.95 (dd, 1H), 2.45 (dd, 1H), 1.25 (t, 3H).

EXAMPLE 2

Preparation of Ethyl 5-Oxo-2-phenyl-3-pyrazolidinecarboxylate (alternatively named Ethyl 1-Phenyl-3-pyrazolidinone-5-carboxylate) using Diethyl Fumarate To a 500-mL four-necked flask equipped with a mechanical stirrer, thermometer, addition funnel, reflux condenser, and nitrogen inlet was charged 150 mL of absolute ethanol, 15.0 g (0.212 mol) of 96% sodium ethoxide in ethanol, and 20.0 mL (0.203 mol) of phenylhydrazine. The orange mixture was treated dropwise with 40.0 mL (0.247 mol) of diethyl fumarate over a period of 75 minutes. The temperature of the reaction mass rose from 28 to a maximum of 37° C. during the addition, and the final temperature was 32° C. The resulting somewhat cloudy, orange solution was held under ambient conditions for 135 minutes. The reaction mixture was then poured into a separatory funnel containing 15.0 mL (0.262 mol) of glacial acetic acid and 700 mL of water. The mixture was extracted with 150 mL of dichloromethane. The extract was dried over magnesium sulfate, filtered, and then concentrated on a rotary evaporator. The resulting brown-yellow oil (41.3 g) was diluted with 100 mL of ether. Several seed crystals were added. The mixture was held for 30 minutes under ambient conditions. It was then cooled to about 0° C. The product was isolated via filtration, washed with 2×10 mL of cold ether, and then air-dried on the filter for about 15 minutes. The product consisted of 9.5 g (20%) of a highly crystalline, white powder. No significant impurities were observed by $^1$H NMR. The filtrate was concentrated to 31 g of a brown oil. Analysis of the oil showed the presence of an additional 7.8 g (16%) of the desired product. Hence, the overall selectivity of the reaction was 36%.

EXAMPLE 3

Preparation of Ethyl 5-Oxo-2-(2-pyridinyl)-3-pyrazolidinecarboxylate (alternatively named Ethyl 1-(2-Pyridinyl-3-pyrazolidinone-5-carboxlate)

To a 200-mL four-necked flask equipped with a mechanical stirrer, thermometer, addition funnel, reflux condenser, and nitrogen inlet was charged 18 mL of absolute ethanol, 18.0 mL (0.0482 mol) of 21% sodium ethoxide in ethanol, and 5.00 g (0.0458 mol) of 2-hydrazinopyridine. The solution was heated to 34° C. It was then treated dropwise with 9.0 mL (0.056 mol) of diethyl maleate over a period of 20 minutes. The temperature of the reaction mass rose to a maximum of 48° C. during the addition. The resulting orange solution was held under ambient conditions for 85 minutes. It was then poured into a separatory funnel containing 4.0 mL (0.070 mol) of glacial acetic acid and 300 mL of water. The mixture was extracted with 2×50 mL of dichloromethane. The extract was dried over magnesium sulfate, filtered, then concentrated on a rotary evaporator. The resulting orange oil (10.7 g) was subjected to flash chromatography on a column of 200 g of silica gel using 4% methanol in chloroform as the eluant (50 mL fractions). Fractions 9–12 were evaporated on a rotary evaporator to give 3.00 g of an orange oil which contained 77% the desired product, 15% chloroform and 8% diethyl 2-ethoxybutanedioate. Fractions 13–17 were concentrated to give 4.75 g of an orange-yellow oil which contained 94% the desired product and 6% chloroform. Fractions 18–21 were concentrated to give 1.51 g of an olive-green oil which contained 80% the desired product and 20% chloroform. Overall yield of the desired product was 8.0 g (74%).

$^1$H NMR (DMSO-d$_6$) δ 10.68 (br, 1H), 8.22 (d, 1H), 7.70 (t, 1H), 6.90 (m, 2H), 5.33 (dd, 1H), 4.17 (q, 2H), 3.05 (dd, 1H), 2.48 (dd, 1H), 1.21 (t, 3H).

EXAMPLE 4

Preparation of Ethyl 2-(2-Chlorophenyl)-5-Oxo-3-pyrazolidinecarboxylate (alternatively named Ethyl 1-(2-Chlorophenyl)-3-pyrazolidinone-5-carboxylate)

To a 250-mL four-necked flask equipped with a mechanical stirrer, thermometer, addition funnel, reflux condenser, and nitrogen inlet was charged 40 mL of absolute ethanol, 40.0 mL (0.107 mol) of 21% sodium ethoxide in ethanol, and 14.5 g (0.102 mol) of (2-chlorophenyl)hydrazine. The purple solution was heated to 35° C. It was then treated dropwise with 19.0 mL (0.117 mol) of diethyl maleate over a period of about 23 minutes. A water/ice bath was used intermittently throughout the addition to moderate the reaction temperature between 35–40° C. The reaction mixture was held at this temperature for 30 minutes. It was then added to a separatory funnel containing 10.0 mL (0.175 mol) of glacial acetic acid and 400 mL of water. The mixture was extracted with 2×100 mL of dichloromethane. The extract was dried over magnesium sulfate, filtered, and then concentrated on a rotary evaporator. The resulting dark brown oil (31.0 g) crystallized upon standing. The material was suspended in 100 mL of ether and the slurry was stirred for about 1 hour. The product was isolated by filtration, washed with 50 mL of ether, and then dried overnight at room temperature in vacuo. The product consisted of 12.5 g (46%) of a crystalline powder. No significant impurities were observed by $^1$H NMR. The filtrate was concentrated to 16.3 g of a brown oil. Analysis of the oil showed the presence of an additional 6.7 g (25%) of the desired product. Hence, the overall selectivity of the reaction was 71%.

$^1$H NMR (DMSO-$d_6$) δ 10.14 (s, 1H), 7.47 (6, 1H), 7.32 (m, 2H), 7.14 (t, 1H), 4.39 (d, 1H), 4.19 (q, 2H), 3.07 (dd, 1H), 2.29 (d, 1H), 1.22 (t, 3H).

EXAMPLE 5

Preparation of Ethyl 2-(3-Chloro-2-pyridinyl)-5-oxo-3-pyrazolidinecarboxylate (alternatively named Ethyl 1-(3-Chloro-2-pyridinyl)-3-pyrazolidinone-5-carboxylate)

To a 2-L four-necked flask equipped with a mechanical stirrer, thermometer, addition funnel, reflux condenser, and nitrogen inlet was charged 250 mL of absolute ethanol and 190 mL (0.504 mol) of 21% sodium ethoxide in ethanol. The mixture was heated to reflux at about 83° C. It was then treated with 68.0 g (0.474 mol) of 3-chloro-2(1H)-pyridinone hydrazone (alternatively named 3-chloro-2-hydrazinopyridine). The mixture was re-heated to reflux over a period of 5 minutes. The yellow slurry was then treated dropwise with 88.0 mL (0.544 mol) of diethyl maleate over a period of 5 minutes. The boil-up rate increased markedly during the addition. By the end of the addition all of the starting material had dissolved. The resulting orange-red solution was held at reflux for 10 minutes. After being cooled to 65° C., the reaction mixture was treated with 50.0 mL (0.873 mol) of glacial acetic acid. A precipitate formed. The mixture was diluted with 650 mL of water, whereupon the precipitate dissolved. The orange solution was cooled in an ice bath. Product began to precipitate at 28° C. The slurry was held at about 2° C. for 2 hours. The product was isolated via filtration, washed with 3×50 mL of 40% aqueous ethanol, and then air-dried on the filter for about 1 hour. The product consisted of 70.3 g (55%) of a highly crystalline, light orange powder. No significant impurities were observed by $^1$H NMR.

$^1$H NMR (DMSO-$d_6$) δ 10.18 (s, 1H), 8.27 (d, 1H), 7.92 (d, 1H), 7.20 (dd, 1H), 4.84 (d, 1H), 4.20 (q, 2H), 2.91 (dd, 1H), 2.35 (d, 1H), 1.22 (t, 3H).

EXAMPLE 6

Preparation of Ethyl 3-Chloro-4,5-dihydro-1-phenyl-1H-pyrazole-5-carboxylate (alternatively named Ethyl 1-Phenyl-3-chloro-2-pyrazoline-5-carboxylate)

EXAMPLE 6A

Using Phosphorus Oxychloride in Acetonitrile in Absence of Base

To a 500-mL four-necked flask equipped with a mechanical stirrer, thermometer, addition funnel, reflux condenser, and nitrogen inlet was charged 150 mL of acetonitrile, 25.0 g (0.107 mol) of ethyl 5-oxo-2-phenyl-3-pyrazolidinecarboxylate, and 11.0 mL (0.118 mol) of phosphorus oxychloride. The light-yellow solution was heated to 78–80° C. for a period of 45 minutes. After being cooled to 54° C., the resulting, deep blue-green mixture was treated dropwise with a solution of 25.0 g (0.298 mol) of sodium bicarbonate in 250 mL of water. An orange oil separated during the 15-minute addition. After being stirred for about 5 minutes, the pH of the mixture was about 1. An additional 10.0 g (0.119 mol) of sodium bicarbonate were added as a solid over a period of about 3 minutes, resulting in a final pH of about 6. The mixture was diluted with 400 mL of water, whereupon the orange oil crystallized. The crystalline mass was broken up with a spatula. The product was isolated via filtration, washed with 4×100 mL of water, and then air-dried on the filter for about 2 hours. The product consisted of 24.5 g (91%) of a fluffy, crystalline, light yellow powder. No significant impurities were observed by $^1$H NMR.

$^1$H NMR (DMSO-$d_6$) δ 2.74 (t, 2H), 6.88 (d, 2H), 6.83 (t, 1H), 5.02 (dd, 1H), 4.14 (q, 2H), 3.68 (dd, 1H), 3.34 (d, 1H), 1.16 (t, 3H).

EXAMPLE 6B

Using Phosphorus Oxychloride in Chloroform in Absence of Base

To a 100-mL two-necked flask equipped with a magnetic stirrer, thermometer, reflux condenser, and nitrogen inlet was charged 50 mL of chloroform, 5.00 g (0.0213 mol) of ethyl 5-oxo-2-phenyl-3-pyrazolidinecarboxylate, 2.10 mL (0.0225 mol) of phosphorus oxychloride, and 2 drops of N,N-dimethylformamide. The red-orange solution was heated to reflux at 64° C. over a period of 60 minutes. The resulting mixture, a yellow-brown liquid and deep green, gummy solids, was held at reflux for 140 minutes. It was then diluted with 100 mL of dichloromethane and transferred to a separatory funnel. The solution was washed twice with 50 mL of 6% aqueous sodium bicarbonate. The organic layer was dried over magnesium sulfate, filtered, then concentrated on a rotary evaporator. The crude product consisted of 1.50 g of an orange oil, which crystallized upon standing. Analysis of the crude product by $^1$H NMR showed it to be about 65% the desired product and 35% starting material. The yield of the desired product was therefore about 18%.

EXAMPLE 6C

Using Phosphorus Oxychloride in Chloroform in Presence of Triethylamine

To a 100-mL two-necked flask equipped with a magnetic stirrer, thermometer, reflux condenser, and nitrogen inlet was charged 20 mL of chloroform, 2.00 g (0.00854 mol) of ethyl 5-oxo-2-phenyl-3-pyrazolidinecarboxylate, 1.30 mL (0.00933 mol) of triethylamine, 2 drops of N,N-dimethylformamide, and 0.0850 mL (0.00912 mol) of phosphorus oxychloride. An immediate and vigorous reaction took place when the phosphorus oxychloride was added. The mixture was heated to reflux at 64° C. for 25 minutes. The resulting yellow solution was diluted with 50 mL of water and then treated with 3.0 g (0.036 mol) of solid sodium bicarbonate. The two-phase mixture was stirred for 50 minutes under ambient conditions. It was then transferred to a separatory funnel and diluted with 100 mL of dichloromethane. The organic layer was separated and then washed in turn with 50 mL of 5.5% aqueous hydrochloric acid and 50 mL of 3.8% aqueous sodium carbonate. The washed, organic layer was dried over magnesium sulfate, filtered, and then concentrated on a rotary evaporator. The crude product consisted of 1.90 g of a yellow oil, which crystallized upon standing. Analysis of the crude product by $^1$H NMR showed it to be about 94% the desired product, 2% starting material and 2% an unidentified impurity. The yield of the desired product was therefore about 83%.

EXAMPLE 7

Preparation of Ethyl 3-Chloro-4,5-dihydro-1-(2-pyridinyl)-1H-pyrazole-5-carboxylate (alternatively named Ethyl 1-(2-Pyridinyl)-3-chloro-2-pyrazoline-5-carboxylate)

To a 250-mL four-necked flask equipped with a mechanical stirrer, thermometer, reflux condenser, and nitrogen inlet was charged 50 mL of acetonitrile, 4.70 g (0.0188 mol) of 5-oxo-2-(2-pyridinyl)-3-pyrazolidinecarboxylate, and 2.00 mL (0.0215 mol) of phosphorus oxychloride. The mixture self-heated from 22 to 33° C. After being held for 60 minutes under ambient conditions, a sample was taken. Analysis by $^1$H NMR showed a 70% conversion of the starting material to the desired product. The mixture was heated to reflux at 85° C. for 80 minutes. The heating mantle was removed. The resulting yellow-orange solution was diluted with 50 mL of water. It was then treated dropwise with 3.9 g (0.049 mol) of 50% aqueous caustic, resulting in a pH of about 7.5. After being stirred for 20 minutes, the pH of the mixture had dropped to about 3. An additional 3.0 g (0.038 mol) of 50% aqueous caustic were added, whereupon the pH increased to about 9.0. A small amount of concentrated hydrochloric acid was added to adjust the pH to about 7.5. The neutralized mixture was transferred to a separatory funnel containing 300 mL of water and 100 mL of dichloromethane. The organic layer was separated, dried over magnesium sulfate, filtered, and then concentrated on a rotary evaporator. The product consisted of 4.10 g (84%) of a pale yellow oil, which crystallized upon standing. The only appreciable impurities observed by $^1$H NMR were 1.0% starting material and 0.6% acetonitrile.

$^1$H NMR (DMSO-d$_6$) δ 8.18 (d, 1H), 8.63 (t, 1H), 8.13 (d, 1H), 7.80 (t, 1H), 5.08 (dd, 1H), 4.11 (m, 2H), 3.65 (dd, 1H), 3.27 (dd, 1H), 1.14 (t, 3H).

EXAMPLE 8

Preparation of Ethyl 3-Chloro-1-(3-chloro-2-pyridinyl)-4,5-dihydro-1H-pyrazole-5-carboxylate (alternatively named Ethyl 1-(3-Chloro-2-pyridinyl)-3-chloro-2-pyrazoline-5-carboxylate)

To a 2-L four-necked flask equipped with a mechanical stirrer, thermometer, reflux condenser, and nitrogen inlet was charged 1000 mL of acetonitrile, 91.0 g (0.337 mol) of ethyl 2-(3-chloro-2-pyridinyl)-5-oxo-3-pyrazolidinecarboxylate, and 35.0 mL (0.375 mol) of phosphorus oxychloride. Upon adding the phosphorus oxychloride, the mixture self-heated from 22 to 25° C. and a precipitate formed. The light-yellow slurry was heated to reflux at 83° C. over a period of 35 minutes, whereupon the precipitate dissolved. The resulting orange solution was held at reflux for 45 minutes, whereupon it had become black-green. The reflux condenser was replaced with a distillation head, and 650 mL of solvent was removed by distillation. A second 2-L four-necked flask equipped with a mechanical stirrer was charged with 130 g (1.55 mol) of sodium bicarbonate and 400 mL of water. The concentrated reaction mixture was added to the sodium bicarbonate slurry over a period of 15 minutes. The resulting, two-phase mixture was stirred vigorously for 20 minutes, at which time gas evolution had ceased. The mixture was diluted with 250 mL of dichloromethane and then was stirred for 50 minutes. The mixture was treated with 11 g of Celite 545® diatomaceous earth and then filtered to remove a black, tarry substance that inhibited phase separation. Since the filtrate was slow to separate into distinct phases, it was diluted with 200 mL of dichloromethane and 200 mL of water and treated with another 15 g of Celite 545®. The mixture was filtered, and the filtrate was transferred to a separatory funnel. The heavier, deep green organic layer was separated. A 50 mL rag layer was refiltered and then added to the organic layer. The organic solution (800 mL) was treated with 30 g of magnesium sulfate and 12 g of silica gel and the slurry was stirred magnetically for 30 minutes. The slurry was filtered to remove the magnesium sulfate and silica gel, which had become deep blue-green. The filter cake was washed with 100 mL of dichloromethane. The filtrate was concentrated on a rotary evaporator. The product consisted of 92.0 g (93%) of a dark amber oil. The only appreciable impurities observed by $^1$H NMR were 1% starting material and 0.7% acetonitrile.

$^1$H NMR (DMSO-d$_6$) δ 8.12 (d, 1H), 7.84 (d, 1H), 7.00 (dd, 1H), 5.25 (dd, 1H), 4.11 (q, 2H), 3.58 (dd, 1H), 3.26 (dd, 1H), 1.15 (t, 3H).

EXAMPLE 9

Preparation of Ethyl 3-Bromo-1-(3-chloro-2-pyridinyl)-4,5-dihydro-1H-pyrazole-5-carboxylate (alternatively named Ethyl 1-(3-Chloro-2-pyridinyl)-3-bromo-2-pyrazoline-5-carboxylate)

EXAMPLE 9A

Using Phosphorus Oxybromide

To a 1-L four-necked flask equipped with a mechanical stirrer, thermometer, reflux condenser, and nitrogen inlet was charged 400 mL of acetonitrile, 50.0 g (0.185 mol) of ethyl 2-(3-chloro-2-pyridinyl)-5-oxo-3-pyrazolidinecarboxylate, and 34.0 g (0.119 mol) of phosphorus oxybromide. The orange slurry was heated to reflux at 83° C. over a period of 20 minutes. The resulting turbid, orange solution was held at reflux for 75 minutes, at which time a dense, tan, crystalline precipitate had formed. The reflux condenser was replaced with a distillation head, and 300 mL of a cloudy, colorless distillate was collected. A second 1-L four-necked flask equipped with a mechanical stirrer was charged with 45 g (0.54 mol) of sodium bicarbonate and 200 mL of water. The concentrated reaction mixture was added to the sodium bicarbonate slurry over a period of 5 minutes. The resulting, two-phase mixture was stirred vigorously for 5 minutes, at which time gas evolution had ceased. The mixture was diluted with 200 mL of dichloromethane, and then was stirred for 75 minutes. The mixture was treated with 5 g of Celite 545®, and then filtered to remove a brown, tarry substance. The filtrate was transferred to a separatory funnel. The brown organic layer (400 mL) was separated, and then was treated with 15 g of magnesium sulfate and 2.0 g of Darco G60 activated charcoal. The resulting slurry was stirred magnetically for 15 minutes and then filtered to remove the magnesium sulfate and charcoal. The green filtrate was treated with 3 g of silica gel and stirred for several minutes. The deep blue-green silica gel was removed by filtration and the filtrate was concentrated on a rotary evaporator. The product consisted of 58.6 g (95%) of a light amber oil, which crystallized upon standing. The only appreciable impurity observed by $^1$H NMR was 0.3% acetonitrile.

$^1$H NMR (DMSO-$d_6$) δ 8.12 (d, 1H), 7.84 (d, 1H), 6.99 (dd, 1H), 5.20 (dd, 1H), 4.11 (q, 2H), 3.60 (dd, 1H), 3.29 (dd, 1H), 1.15 (t, 3H).

EXAMPLE 9B

Using Phosphorus Pentabromide

To a 1-L four-necked flask equipped with a mechanical stirrer, thermometer, reflux condenser, and nitrogen inlet was charged 330 mL of acetonitrile, 52.0 g (0.193 mol) of ethyl 2-(3-chloro-2-pyridinyl)-5-oxo-3-pyrazolidinecarboxylate, and 41.0 g (0.0952 mol) of phosphorus pentabromide. The orange slurry was heated to reflux at 84° C. over a period of 20 minutes. The resulting brick-red mixture was held at reflux for 90 minutes, at which time a dense, tan, crystalline precipitate had formed. The reflux condenser was replaced with a distillation head, and 220 mL of a cloudy, colorless distillate was collected. A second 1-L four-necked flask equipped with a mechanical stirrer was charged with 40 g (0.48 mol) of sodium bicarbonate and 200 mL of water. The concentrated reaction mixture was added to the sodium bicarbonate slurry over a period of 5 minutes. The resulting, two-phase mixture was stirred vigorously for 10 minutes, at which time gas evolution had ceased. The mixture was diluted with 200 mL of dichloromethane, and then was stirred for 10 minutes. The mixture was treated with 5 g of Celite 545®, and then filtered to remove a purple, tarry substance. The filter cake was washed with 50 mL of dichloromethane. The filtrate was transferred to a separatory funnel. The purple-red organic layer (400 mL) was separated, then was treated with 15 g of magnesium sulfate and 2.2 g of Darco G60 activated charcoal. The slurry was stirred magnetically for 40 minutes. The slurry was filtered to remove the magnesium sulfate and charcoal. The filtrate was concentrated on a rotary evaporator. The product consisted of 61.2 g (95%) of a dark amber oil, which crystallized upon standing. The only appreciable impurity observed by $^1$H NMR was 0.7% acetonitrile.

$^1$H NMR (DMSO-$d_6$) δ 8.12 (d, 1H), 7.84 (d, 1H), 6.99 (dd, 1H), 5.20 (dd, 1H), 4.11 (q 2H), 3.60 (dd, 1H), 3.29 (dd, 1H), 1.15 (t, 3H).

EXAMPLE 10

Preparation of Ethyl 3-Chloro-1-phenyl-1H-pyrazole-5-carboxylate (alternatively named Ethyl 1-Phenyl-3-chloropyrazole-5-carboxylate)

EXAMPLE 10A

Using Hydrogen Peroxide

To a 100-mL two-necked flask equipped with a magnetic stirrer, thermometer, reflux condenser, and nitrogen inlet was charged 1.50 g (0.00594 mol) of ethyl 3-chloro-4,5-dihydro-1-phenyl-1H-pyrazole-5-carboxylate and 15 mL of acetonitrile. The mixture was heated to 80° C. It was then treated with 0.700 mL (0.00685 mol) of 30% aqueous hydrogen peroxide. The mixture was held at 78–80° C. for 5 hours. The reaction mass was then added to 70 mL of water. The precipitated product was isolated via filtration, and then washed with 15 mL of water. The wet cake was dissolved in 100 mL of dichloromethane. The solution was dried over magnesium sulfate, filtered, and then concentrated on a rotary evaporator. The product consisted of 1.24 g (about 79%) of an orange oil, which crystallized upon standing. The product was about 95% pure based upon $^1$H NMR.

$^1$H NMR (DMSO-$d_6$) δ 7.50 (s, 5H), 7.20 (s, 1H), 7.92 (d, 1H), 4.18 (q, 2H), 1.14 (t, 3H).

EXAMPLE 10B

Using Manganese Dioxide

To a 100-mL two-necked flask equipped with a magnetic stirrer, thermometer, reflux condenser, and nitrogen inlet was charged 3.00 g (0.0119 mol) of ethyl 3-chloro-4,5-dihydro-1-phenyl-1H-pyrazole-5-carboxylate, 25 mL of chloroform, and 2.50 g (0.0245 mol) of activated manganese dioxide. The mixture was heated to reflux at 62° C. for a period of 1 hour. Analysis of a sample of the reaction mass by $^1$H NMR showed about 6% conversion of the starting material to mainly the desired ethyl 1-phenyl-3-chloropyrazole-5-carboxylate. The mixture was held for another 5 hours at reflux. Analysis of a second sample showed about 9% conversion.

EXAMPLE 10C

Using Sodium Hypochlorite

To a 100-mL two-necked flask equipped with a magnetic stirrer, thermometer, reflux condenser, and nitrogen inlet was charged 1.00 g (0.00396 mol) of ethyl 3-chloro-4,5-dihydro-1-phenyl-1H-pyrazole-5-carboxylate, 10 mL of acetonitrile, 0.55 g (0.0040 mol) of sodium dihydrogen phosphate monohydrate, and 5.65 g (0.00398 mol) of 5.25% aqueous sodium hypochlorite. The orange solution was held under ambient conditions for 85 minutes. Analysis of a sample of the reaction mass by $^1$H NMR showed about 71% conversion of the starting material to two main products. The solution was heated to 60° C. for 60 minutes. Analysis of a second sample showed no increase in conversion from the first sample. The reaction mixture was treated with an additional 3.00 g (0.00211 mol) of 5.25% aqueous sodium hypochlorite. After being held for 60 minutes at 60° C., the reaction mass was added to 100 mL of water. The mixture was extracted with 100 mL of dichloromethane. The extract was separated, dried over magnesium sulfate, filtered, and then concentrated on a rotary evaporator. The crude product consisted of 0.92 g of a red-orange oil. $^1$H NMR showed the crude product to consist mainly of ethyl 3-chloro-1-(4-chlorophenyl)-4,5-dihydro-1H-pyrazole-5-carboxylate (alternatively named ethyl 1-(4-chlorophenyl)-3-chloro-2-pyrazoline-5-carboxylate) and ethyl 3-chloro-1-(2-chlorophenyl)-4,5-dihydro-1H-pyrazole-5-carboxylate (alternatively named ethyl 1-(2-chlorophenyl)-3-chloro-2-pyrazoline-5-carboxylate) in a ratio of 2:1. The isomer could be separated by chromatography on silica gel using 10% ethyl acetate in hexanes as the eluant.

$^1$H NMR for ethyl 3-chloro-1-(4-chlorophenyl)-4,5-dihydro-1H-pyrazole-5-carboxylate (DMSO-$d_6$) δ 7.28 (d, 2H), 6.89 (d, 2H), 5.08 (dd, 1H), 4.14 (q, 2H), 3.71 (dd, 1H) 3.37 (dd, 1H), 1.16 (t, 3H). $^1$H NMR for ethyl 3-chloro-1-(2-chlorophenyl)-4,5-dihydro-1H-pyrazole-5-carboxylate (DMSO-$d_6$) δ 7.41 (d, 1H), 7.30 (m, 2H), 7.14 (m, 1H), 5.22 (dd, 1H), 3.90 (q, 2H), 3.68 (dd, 1H), 3.38 (dd, 1H), 0.91 (t, 3H).

EXAMPLE 11

Preparation of Ethyl 3-Chloro-1-(3-chloro-2-pyridinyl)-1H-pyrazole-5-carboxylate (alternatively named Ethyl 1-(3-Chloro-2-pyridinyl)-3-chloropyrazole-5-carboxylate)

To a 2-L four-necked flask equipped with a mechanical stirrer, thermometer, reflux condenser, and nitrogen inlet was charged 99.5 g (0.328 mol) of 95% pure ethyl 3-chloro-1-(3-chloro-2-pyridinyl)-4,5-dihydro-1H-pyrazole-5-carboxylate, 1000 mL of acetonitrile and 35.0 mL (0.661 mol) of 98% sulfuric acid. The mixture self-heated from 22 to 35° C. upon adding the sulfuric acid. After being stirred for several minutes, the mixture was treated with 140 g (0.518 mol) of potassium persulfate. The slurry was heated to reflux at 84° C. for 4.5 hours. The resulting orange slurry was filtered while still warm (50–65° C.) to remove a fine, white precipitate. The filter cake was washed with 50 mL of acetonitrile. The filtrate was concentrated to about 500 mL on a rotary evaporator. A second 2-L four-necked flask equipped with a mechanical stirrer was charged with 1250 mL of water. The concentrated reaction mass was added to the water over a period of about 5 minutes. The product was isolated via filtration, washed with 3×125 mL of 25% aqueous acetonitrile, washed once with 100 mL of water, and then dried overnight in vacuo at room temperature. The product consisted of 79.3 g (82%) of a crystalline, orange powder. The only appreciable impurities observed by $^1$H NMR were about 1.9% water and 0.6% acetonitrile.

$^1$H NMR (DMSO-d$_6$) δ 8.59 (d, 1H), 8.38 (d, 1H), 7.71 (dd, 1H), 7.31 (s, 1H), 4.16 (q, 2H), 1.09 (t, 3H).

EXAMPLE 12

Preparation of Ethyl 3-Bromo-1-(3-chloro-2-pyridinyl)-1H-pyrazole-5-carboxylate (alternatively named Ethyl 1-(3-Chloro-2-pyridinyl)-3-bromopyrazole-5-carboxylate)

To a 1-L four-necked flask equipped with a mechanical stirrer, thermometer, reflux condenser, and nitrogen inlet was charged 40.2 g (0.121 mol) of ethyl 3-bromo-1-(3-chloro-2-pyridinyl)-4,5-dihydro-1H-pyrazole-5-carboxylate, 300 mL of acetonitrile and 13.0 mL (0.245 mol) of 98% sulfuric acid. The mixture self-heated from 22 to 36° C. upon adding the sulfuric acid. After being stirred for several minutes, the mixture was treated with 48.0 g (0.178 mol) of potassium persulfate. The slurry was heated to reflux at 84° C. for 2 hours. The resulting orange slurry was filtered while still warm (50–65° C.) to remove a white precipitate. The filter cake was washed with 2×50 mL of acetonitrile. The filtrate was concentrated to about 200 mL on a rotary evaporator. A second 1-L four-necked flask equipped with a mechanical stirrer was charged with 400 mL of water. The concentrated reaction mass was added to the water over a period of about 5 minutes. The product was isolated via filtration, washed with 100 mL of 20% aqueous acetonitrile, washed with 75 mL of water, and then air-dried on the filter for 1 hour. The product consisted of 36.6 g (90%) of a crystalline, orange powder. The only appreciable impurities observed by $^1$H NMR were about 1% of an unknown and 0.5% acetonitrile.

$^1$H NMR (DMSO-d$_6$) δ 8.59 (d, 1H), 8.39 (d, 1H), 7.72 (dd, 1H), 7.35 (s, 1H), 4.16 (q, 2H), 1.09 (t, 3H).

EXAMPLE 13

Preparation of 3-Chloro-1-(3-chloro-2-pyridinyl-1H-pyrazole-5-carboxylic acid (alternatively named 1-(3-Chloro-2-pyridinyl-3-chloropyrazole-5-carboxylic acid)

To a 1-L four-necked flask equipped with a mechanical stirrer, thermometer, and nitrogen inlet was charged 79.3 g (0.270 mol) of 97.5% ethyl 3-chloro-1-(3-chloro-2-pyridinyl)-1H-pyrazole-5-carboxylate, 260 mL of methanol, 140 mL of water, and 13.0 g (0.325 mol) of sodium hydroxide pellets. The mixture self-heated from 22 to 35° C. and the starting material began to dissolve upon adding the sodium hydroxide. After being stirred for 45 minutes under ambient conditions, all of the starting material had dissolved. The resulting deep orange-brown solution was concentrated to about 250 mL on a rotary evaporator. The concentrated reaction mixture was then diluted with 400 mL of water. The aqueous solution was extracted with 200 mL of ether. The aqueous layer was transferred to a 1-L Erlenmeyer flask equipped with a magnetic stirrer. The solution was then treated dropwise with 36.0 g (0.355 mol) of concentrated hydrochloric acid over a period of about 10 minutes. The product was isolated via filtration, reslurried with 2×200 mL of water, cover washed once with 100 mL of water, and then air-dried on the filter for 1.5 hours. The product consisted of 58.1 g (83%) of a crystalline, light brown powder. About 0.7% ether was the only appreciable impurity observed by $^1$H NMR.

$^1$H NMR (DMSO-d$_6$) δ 13.95 (brs, 1H), 8.56 (d, 1H), 8.25 (d, 1H), 7.68 (dd, 1H), 7.20 (s, 1H).

EXAMPLE 14

Preparation of 3-Bromo-1-(3-chloro-2-pyridinyl)-1H-pyrazole-carboxylic acid (alternatively named 1-(3-Chloro-2-pyridinyl -3-bromopyrazole-5-carboxylic acid)

To a 300-mL four-necked flask equipped with a mechanical stirrer, thermometer, and nitrogen inlet was charged 25.0 g (0.0756 mol) of 98.5% pure ethyl 3-bromo-1-(3-chloro-2-pyridinyl)-1H-pyrazole-5-carboxylate, 75 mL of methanol, 50 mL of water, and 3.30 g (0.0825 mol) of sodium hydroxide pellets. The mixture self-heated from 29 to 34° C. and the starting material began to dissolve upon adding the sodium hydroxide. After being stirred for 90 minutes under ambient conditions, all of the starting material had dissolved. The resulting dark orange solution was concentrated to about 90 mL on a rotary evaporator. The concentrated reaction mixture was then diluted with 160 mL of water. The aqueous solution was extracted with 100 mL of ether. The aqueous layer was transferred to a 500-mL Erlenmeyer flask equipped with a magnetic stirrer. The solution was then treated dropwise with 8.50 g (0.0839 mol) of concentrated hydrochloric acid over a period of about 10 minutes. The product was isolated via filtration, reslurried with 2×40 mL of water, cover washed once with 25 mL of water, and then air-dried on the filter for 2 hours. The product consisted of 20.9 g (91%) of a crystalline, tan powder. The only appreciable impurities observed by $^1$H NMR were about 0.8% of an unknown and 0.7% ether.

$^1$H NMR (DMSO-d$_6$) δ 13.95 (br s, 1H), 8.56 (d, 1H), 8.25 (d, 1H), 7.68 (dd, 1H), 7.25 (s, 1H).

EXAMPLE 15

Preparation of ethyl 3-bromo-1-(3-chloro-2-pyridinyl)-4,5-dihydro-1H-pyrazole-5-carboxylate from ethyl 3-chloro-1-(3-chloro-2-pyridinyl)-4,5-dihydro-1H-pyrazole-5-carboxylate using hydrogen bromide Hydrogen bromide was passed through a solution of ethyl 3-chloro-1-(3-chloro-2-pyridinyl)-4,5-dihydro-1H-pyrazole-5-carboxylate (8.45 g, 29.3 mmol) in dibromomethane (85 mL). After 90 minutes the gas flow was terminated, and the reaction mixture was washed with aqueous sodium bicarbonate solution (100 mL). The organic phase was dried and evaporated under reduced pressure to give the title product as an oil (9.7 g, 99% yield), which crystallized on standing.

$^1$H NMR (CDCl$_3$) δ 8.07 (dd, J=1.6, 4.8 Hz, 1H), 7.65 (dd, J=1.6, 7.8 Hz, 1H), 6.85 (dd, J=4.7, 7.7 Hz, 1H), 5.25 (X of ABX, 1H, J=9.3, 11.9 Hz), 4.18 (q, 2H), 3.44 (½ of AB in ABX pattern, J=11.7, 17.3 Hz, 1H), 3.24 (1/2 of AB in ABX pattern, J=9.3, 17.3 Hz, 1H), 1.19 (t, 3H).

The following Example 16 illustrates the preparation of ethyl 1-(3-chloro-2-pyridinyl)-4,5-dihydro-3-[[(4-methylphenyl)sulfonyl]oxy]-1H-pyrazole-5-carboxylate, which can be used to prepare ethyl 3-bromo-1-(3-chloro-2-pyridinyl)-4,5-dihydro-1H-pyrazole-5-carboxylate by procedures similar to that described in Example 15.

EXAMPLE 16

Preparation of ethyl 1-(3-chloro-2-pyridinyl)-4,5-dihydro-3-[[(4-methylphenyl)sulfonyl]oxy]-1H-pyrazole-5-carboxylate Triethylamine (3.75 g, 37.1 mmol) was added dropwise to a mixture of ethyl 2-(3-chloro-2-pyridinyl)-5-oxo-3-pyrazolidinecarboxylate (10.0 g, 37.1 mmol) and p-toluenesulfonyl chloride (7.07 g, 37.1 mmol) in dichloromethane (100 mL) at 0° C. Further portions of p-toluenesulfonyl chloride (0.35 g, 1.83 mmol) and triethylamine (0.19 g, 1.88 mmol) were added. The reaction mixture was then allowed to warm to room temperature and was stirred overnight. The mixture was then diluted with dichloromethane (200 mL) and washed with water (3×70 mL). The organic phase was dried and evaporated to leave the title product as an oil (13.7 g, 87% yield), which slowly formed crystals. Product recrystallized from ethyl acetate/hexanes melted at 99.5–100° C.

IR (nujol): 1740, 1638, 1576, 1446, 1343, 1296, 1228, 1191, 1178, 1084, 1027, 948, 969, 868, 845 cm$^{-1}$.

$^1$H NMR (CDCl$_3$) δ 8.01 (dd, J=1.4, 4.6 Hz, 1H), 7.95 (d, J=8.4 Hz, 2H), 7.56 (dd, J=1.6, 7.8 Hz, 1H), 7.36 (d, J=8.4 Hz, 2H), 6.79 (dd, J=4.6, 7.7 Hz, 1H), 5.72 (X of ABX, J=9, 11.8 Hz, 1H), 4.16 (q, 2H), 3.33 (½ of AB in ABX pattern, J=17.5, 11.8 Hz, 1H), 3.12 (½ of AB in ABX pattern, J=17.3,9 Hz, 1H), 2.45 (s, 3H), 1.19 (t, 3H).

By the procedures described herein together with methods known in the art, the following compounds of Tables 1 to 3 can be prepared. The following abbreviations are used in the Tables: t is tertiary, s is secondary, n is normal, i is iso, Me is methyl, Et is ethyl, Pr is propyl, i-Pr is isopropyl and t-Bu is tertiary butyl.

TABLE 1

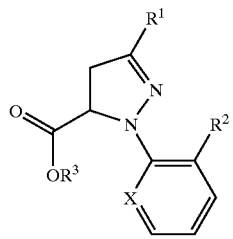

| X is N | | X is CH | | X is CCl | | X is CBr | |
|---|---|---|---|---|---|---|---|
| R$^2$ | R$^3$ | R$^2$ | R$^3$ | R$^2$ | R$^3$ | R$^2$ | R$^3$ |
| R$^1$ is Cl | | | | | | | |
| Cl | H  | Br | H  | Cl | H  | Br | H  | Cl | H  | Br | H  | Cl | H  | Br | H  |
| Cl | Me | Br | Me | Cl | Me | Br | Me | Cl | Me | Br | Me | Cl | Me | Br | Me |
| Cl | Et | Br | Et | Cl | Et | Br | Et | Cl | Et | Br | Et | Cl | Et | Br | Et |
| Cl | n-Pr | Br | n-Pr | Cl | n-Pr | Br | n-Pr | Cl | n-Pr | Br | n-Pr | Cl | n-Pr | Br | n-Pr |
| Cl | i-Pr | Br | i-Pr | Cl | i-Pr | Br | i-Pr | Cl | i-Pr | Br | i-Pr | Cl | i-Pr | Br | i-Pr |
| Cl | n-Bu | Br | n-Bu | Cl | n-Bu | Br | n-Bu | Cl | n-Bu | Br | n-Bu | Cl | n-Bu | Br | n-Bu |
| Cl | i-Bu | Br | i-Bu | Cl | i-Bu | Br | i-Bu | Cl | i-Bu | Br | i-Bu | Cl | i-Bu | Br | i-Bu |
| Cl | s-Bu | Br | s-Bu | Cl | s-Bu | Br | s-Bu | Cl | s-Bu | Br | s-Bu | Cl | s-Bu | Br | s-Bu |
| Cl | t-Bu | Br | t-Bu | Cl | t-Bu | Br | t-Bu | Cl | t-Bu | Br | t-Bu | Cl | t-Bu | Br | t-Bu |
| R$^1$ is Br | | | | | | | |
| Cl | H  | Br | H  | Cl | H  | Br | H  | Cl | H  | Br | H  | Cl | H  | Br | H  |
| Cl | Me | Br | Me | Cl | Me | Br | Me | Cl | Me | Br | Me | Cl | Me | Br | Me |
| Cl | Et | Br | Et | Cl | Et | Br | Et | Cl | Et | Br | Et | Cl | Et | Br | Et |
| Cl | n-Pr | Br | n-Pr | Cl | n-Pr | Br | n-Pr | Cl | n-Pr | Br | n-Pr | Cl | n-Pr | Br | n-Pr |
| Cl | i-Pr | Br | i-Pr | Cl | i-Pr | Br | i-Pr | Cl | i-Pr | Br | i-Pr | Cl | i-Pr | Br | i-Pr |
| Cl | n-Bu | Br | n-Bu | Cl | n-Bu | Br | n-Bu | Cl | n-Bu | Br | n-Bu | Cl | n-Bu | Br | n-Bu |
| Cl | i-Bu | Br | i-Bu | Cl | i-Bu | Br | i-Bu | Cl | i-Bu | Br | i-Bu | Cl | i-Bu | Br | i-Bu |
| Cl | s-Bu | Br | s-Bu | Cl | s-Bu | Br | s-Bu | Cl | s-Bu | Br | s-Bu | Cl | s-Bu | Br | s-Bu |
| Cl | t-Bu | Br | t-Bu | Cl | t-Bu | Br | t-Bu | Cl | t-Bu | Br | t-Bu | Cl | t-Bu | Br | t-Bu |

TABLE 2

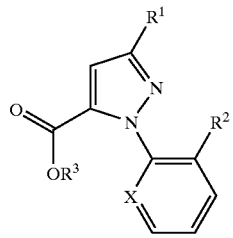

| X is N | | | | X is CH | | | | X is CCl | | | | X is CBr | | | |
|---|---|---|---|---|---|---|---|---|---|---|---|---|---|---|---|
| $R^2$ | $R^3$ | $R^2$ | $R^3$ | $R^2$ | $R^3$ | $R^2$ | $R^3$ | $R^2$ | $R^3$ | $R^2$ | $R^3$ | $R^2$ | $R^3$ | $R^2$ | $R^3$ |
| | | | | | | | $R^1$ is Cl | | | | | | | | |
| Cl | H | Br | H | Cl | H | Br | H | Cl | H | Br | H | Cl | H | Br | H |
| Cl | Me | Br | Me | Cl | Me | Br | Me | Cl | Me | Br | Me | Cl | Me | Br | Me |
| Cl | Et | Br | Et | Cl | Et | Br | Et | Cl | Et | Br | Et | Cl | Et | Br | Et |
| Cl | n-Pr | Br | n-Pr | Cl | n-Pr | Br | n-Pr | Cl | n-Pr | Br | n-Pr | Cl | n-Pr | Br | n-Pr |
| Cl | i-Pr | Br | i-Pr | Cl | i-Pr | Br | i-Pr | Cl | i-Pr | Br | i-Pr | Cl | i-Pr | Br | i-Pr |
| Cl | n-Bu | Br | n-Bu | Cl | n-Bu | Br | n-Bu | Cl | n-Bu | Br | n-Bu | Cl | n-Bu | Br | n-Bu |
| Cl | i-Bu | Br | i-Bu | Cl | i-Bu | Br | i-Bu | Cl | i-Bu | Br | i-Bu | Cl | i-Bu | Br | i-Bu |
| Cl | s-Bu | Br | s-Bu | Cl | s-Bu | Br | s-Bu | Cl | s-Bu | Br | s-Bu | Cl | s-Bu | Br | s-Bu |
| Cl | t-Bu | Br | t-Bu | Cl | t-Bu | Br | t-Bu | Cl | t-Bu | Br | t-Bu | Cl | t-Bu | Br | t-Bu |
| | | | | | | | $R^1$ is Br | | | | | | | | |
| Cl | H | Br | H | Cl | H | Br | H | Cl | H | Br | H | Cl | H | Br | H |
| Cl | Me | Br | Me | Cl | Me | Br | Me | Cl | Me | Br | Me | Cl | Me | Br | Me |
| Cl | Et | Br | Et | Cl | Et | Br | Et | Cl | Et | Br | Et | Cl | Et | Br | Et |
| Cl | n-Pr | Br | n-Pr | Cl | n-Pr | Br | n-Pr | Cl | n-Pr | Br | n-Pr | Cl | n-Pr | Br | n-Pr |
| Cl | i-Pr | Br | i-Pr | Cl | i-Pr | Br | i-Pr | Cl | i-Pr | Br | i-Pr | Cl | i-Pr | Br | i-Pr |
| Cl | n-Bu | Br | n-Bu | Cl | n-Bu | Br | n-Bu | Cl | n-Bu | Br | n-Bu | Cl | n-Bu | Br | n-Bu |
| Cl | i-Bu | Br | i-Bu | Cl | i-Bu | Br | i-Bu | Cl | i-Bu | Br | i-Bu | Cl | i-Bu | Br | i-Bu |
| Cl | s-Bu | Br | s-Bu | Cl | s-Bu | Br | s-Bu | Cl | s-Bu | Br | s-Bu | Cl | s-Bu | Br | s-Bu |
| Cl | t-Bu | Br | t-Bu | Cl | t-Bu | Br | t-Bu | Cl | t-Bu | Br | t-Bu | Cl | t-Bu | Br | t-Bu |

TABLE 3

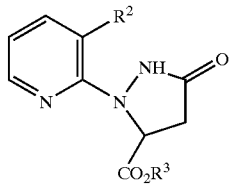

| $R^2$ | $R^3$ | $R^2$ | $R^3$ | $R^2$ | $R^3$ | $R^2$ | $R^3$ | $R^2$ | $R^3$ | $R^2$ | $R^3$ |
|---|---|---|---|---|---|---|---|---|---|---|---|
| Cl | H | Cl | n-Pr | Cl | i-Bu | Br | H | Br | n-Pr | Br | i-Bu |
| Cl | Me | Cl | i-Pr | Cl | s-Bu | Br | Me | Br | i-Pr | Br | s-Bu |
| Cl | Et | Cl | n-Bu | Cl | t-Bu | Br | Et | Br | n-Bu | Br | t-Bu |

Utility

The compounds of Formulae I, I and 4 are useful as synthetic intermediates for preparing a compound of Formula III

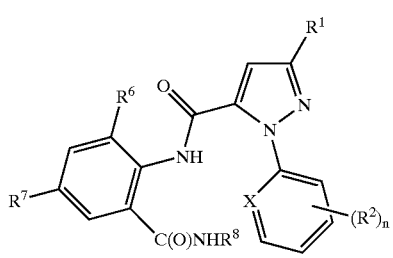

III wherein X, $R^1$, $R^2$ and n are defined as above; $R^6$ is $CH_3$, Cl or Br; $R^7$ is F, Cl, Br, I or $CF_3$; and $R^8$ is $C_1$–$C_4$ alkyl.

Compounds of Formula III are useful as insecticides.

Compounds of Formula III can be prepared from compounds of Formula II (and in turn from compounds of Formula 4 and I) by the processes outlined in Schemes 5–7.

Coupling of a pyrazolecarboxylic acid of Formula IIa (a compound of Formula II wherein $R^3$ is H) with an anthranilic acid of Formula 5 provides the benzoxazinone of Formula 6. In Scheme 5, a benzoxazinone of Formula 6 is prepared directly via sequential addition of methanesulfonyl chloride in the presence of a tertiary amine such as triethylamine or pyridine to a pyrazolecarboxylic acid of Formula IIa, followed by the addition of an anthranilic acid of Formula 5, followed by a second addition of tertiary amine and methanesulfonyl chloride. This procedure generally affords good yields of the benzoxazinone.

Scheme 5

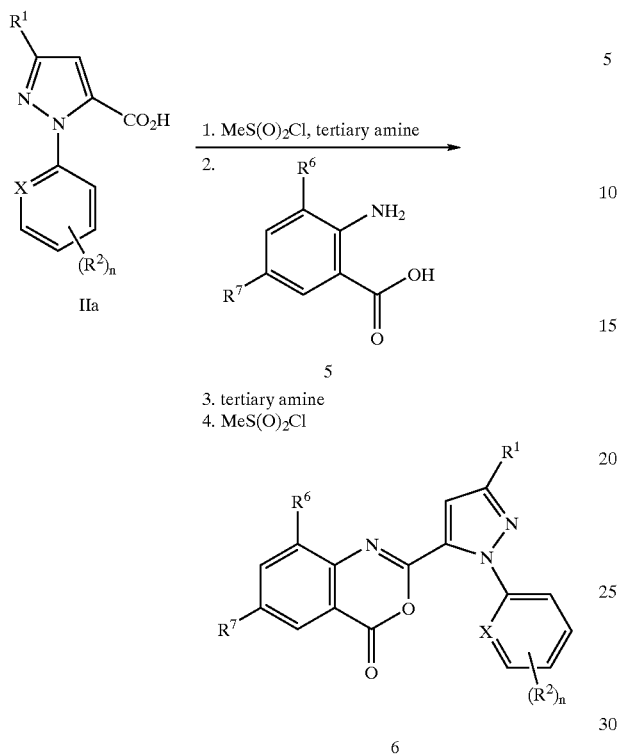

Scheme 6 depicts an alternate preparation for benzoxazinones of Formula 6 involving coupling of a pyrazole acid chloride of Formula 8 with an isatoic anhydride of Formula 7 to provide the Formula 6 benzoxazinone directly.

Scheme 6

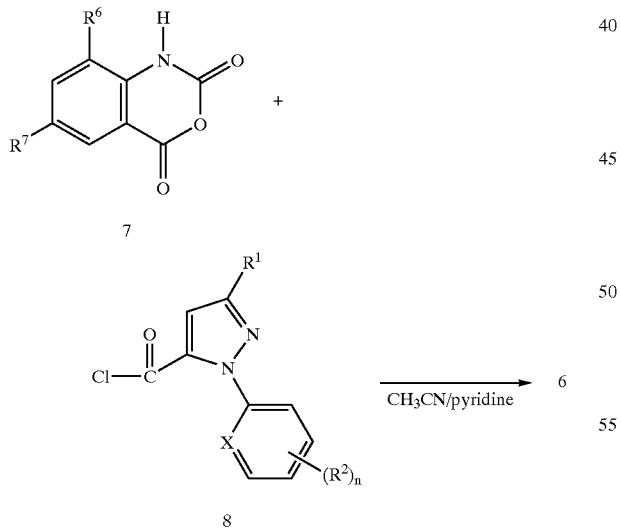

Solvents such as pyridine or pyridine/acetonitrile are suitable for this reaction. The acid chlorides of Formula 8 are available from the corresponding acids of Formula IIa by known procedures such as chlorination with thionyl chloride or oxalyl chloride.

Compounds of Formula III can be prepared by the reaction of benzoxazinones of Formula 6 with $C_1$–$C_4$ alkyl amines as outlined in Scheme 7. The reaction can be run neat or in a variety of suitable solvents including tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095–2103 and references cited within. See also Coppola, *J. Heterocyclic Chemistry* 1999, 36, 563–588.

Scheme 7

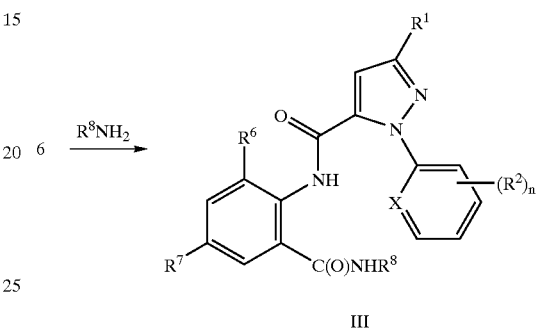

What is claimed is:

1. A compound of Formula I

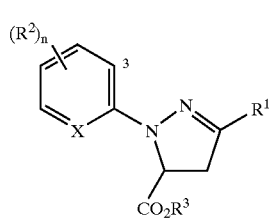

wherein $R^1$ is halogen;

each $R^2$ is independently $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_3$–$C_6$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

$R^3$ is H or $C_1$–$C_4$ alkyl;

X is N or $CR^4$;

$R^4$ is H or $R^2$; and n is 0 to 3, provided when X is CH then n is at least 1.

2. A compound of claim 1 wherein n is 1 to 3.

3. A compound of claim 1 wherein $R^1$ is Cl or Br; each $R^2$ is independently Cl or Br, and one $R^2$ is at the 3-position; and X is N.

4. A method for preparing a compound of claim 1 comprising
(1) treating a compound of Formula 4

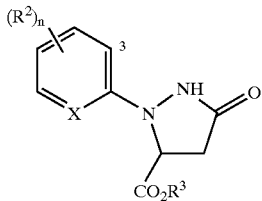

4 wherein $R^3$ is $C_1$–$C_4$ alkyl;
with a halogenating agent to form a compound of Formula I; and when preparing compounds of Formula I wherein $R^3$ is H
(2) converting the compound formed in (1) to a compound wherein $R^3$ is H.

5. The method of claim 4 wherein n is 1 to 3.

6. The method of claim 4 wherein $R^1$ is Cl or Br; each $R^2$ is independently Cl or Br, and one $R^2$ is at the 3-position; $R^3$ is $C_1$–$C_4$ alkyl; and X is N.

7. The method of claim 6 wherein the halogenating agent is a phosphorus oxyhalide or a phosphorus pentahalide.

8. The method of claim 7 wherein step (1) is carried out in the absence of a base using acetonitrile as the solvent.

* * * * *